United States Patent [19]

Toja et al.

[11] 4,435,417
[45] * Mar. 6, 1984

[54] ANTIINFLAMMATORY 3H-NAPHTHO[1,2-D]IMIDAZOLES

[75] Inventors: Emilio Toja, Milan; Amedeo Omodei-Sale', Voghera; Domenica Selva, Milan, all of Italy

[73] Assignee: Gruppo Lepetit S.p.A., Milan, Italy

[*] Notice: The portion of the term of this patent subsequent to Jul. 20, 1999 has been disclaimed.

[21] Appl. No.: 391,653

[22] Filed: Jun. 24, 1982

Related U.S. Application Data

[63] Continuation of Ser. No. 236,473, Feb. 20, 1981, abandoned, which is a continuation-in-part of Ser. No. 104,490, Dec. 17, 1979, abandoned.

[51] Int. Cl.$^3$ .................. A61K 31/415; C07D 235/18
[52] U.S. Cl. ............................ 424/273 B; 548/326; 564/428
[58] Field of Search ............... 548/326; 424/273 B

[56] References Cited

U.S. PATENT DOCUMENTS 4,340,607 7/1982 Toja et al. ............... 424/273 B

FOREIGN PATENT DOCUMENTS 1137625 10/1962 Fed. Rep. of Germany .
50-40626 4/1975 Japan ..................... 548/326
20780 of 1906 United Kingdom ............ 548/326

OTHER PUBLICATIONS

Yoshida, Z., et al., *Chemical Abstracts*, 48: 11398c (1954) [*J. Chem. Soc., Japan*, Ind. Chem. Sect. 55, 354-356 (1952)].
Omodei-Sale, A., et al., *Chemical Abstracts*, 85: 192731p (1976) [German OLS 2,551,868, 8/12/76].

*Primary Examiner*—Richard A. Schwartz
*Attorney, Agent, or Firm*—William J. Stein; Stephen L. Nesbitt; Gary D. Street

[57] ABSTRACT

3H-naphtho[1,2-d]imidazole derivatives of formula

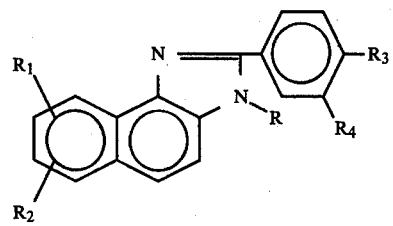

wherein R stands for $(C_{1-6})$alkyl, $(C_{3-6})$alkenyl, $(C_{3-6})$alkynyl or $(C_{3-7})$cycloalkyl, $R_1$ and $R_2$, each independently may represent hydrogen, halogen, $(C_{1-4})$alkyl, $(C_{1-4})$alkylthio, $(C_{1-4})$alkoxy or halo$(C_{1-4})$alkoxy, $R_3$ stands for hydrogen, hydroxy, methoxy, ethoxy, or mono- or di-methylamino, and $R_4$ represents hydrogen or $(C_{1-4})$alkyl.

Also described and claimed are their use as antiinflammatory agents and the pharmaceutical compositions containing them.

15 Claims, No Drawings

ANTIINFLAMMATORY 3H-NAPHTHO[1,2-D]IMIDAZOLES

CROSS-REFERENCE TO RELATED APPLICATION

This is a continuation, of application Ser. No. 236,473, filed Feb. 20, 1981, now abandoned, which is a continuation-in-part of U.S. patent application Ser. No. 104,490 filed on Dec. 17, 1979, now abandoned.

The present invention relates to novel 3H-naphtho[1,2-d]imidazole derivatives of the following general formula I

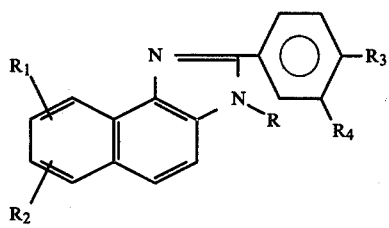

wherein R stands for $(C_{1-6})$alkyl, $(C_{3-6})$alkenyl, $(C_{3-6})$alkynyl or $(C_{3-7})$cycloalkyl, $R_1$ and $R_2$, each independently may represent hydrogen, halogen $(C_{1-4})$alkyl, $(C_{1-4})$alkylthio, $(C_{1-4})$alkoxy or halo$(C_{1-4})$alkoxy, $R_3$ stands for hydrogen, hydroxy, methoxy, ethoxy or mono- or di-methylamino and $R_4$ stands for hydrogen or lower alkyl; with the proviso that when R stands for an ethyl radical, one of $R_1$ and $R_2$ is hydrogen and the other is a methoxy group, and $R_4$ is hydrogen, $R_3$ cannot be a dimethylamino group; and salts therewith of pharmaceutically acceptable acids. The novel compounds of the present invention possess antiinflammatory, analgesic, and antipyretic utility. The compound excluded from the present invention by the above proviso is known from German Pat. No. 1,137,625 which reports several thiazole, oxazole and imidazole derivatives with photoconductive properties, that can suitably be employed for electrophotographic reproduction. A compound as in formula I but wherein R is methyl, $R_1$ and $R_2$ are hydrogen, $R_4$ is hydrogen and $R_3$ is a nitro group is known from the article by J. W. Lown and M. H. Akhtor published in Can. J. Chem. 49, (1971) 1610, where the authors discuss the mechanisms involved in the reaction of 1-nitroso-2-naphthylamine with 3-aroyl-aziridines.

Moreover, other naphthoimidazoles, substituted in the 2-position by an alkyl group, are described in U.S. Pat. No. 3,046,116 where it is said that these compounds can be conveniently used in the production of printing plates. As used herein the term "$(C_{1-4})$alkyl" and the alkyl portion of other hereinlisted radicals containing a $(C_{1-4})$alkyl moiety identifies a straight or branched alkyl radical having from 1 to 4 carbon atoms such as methyl, ethyl, propyl, 1-methylethyl, butyl, 1-methylpropyl, 2-methylpropyl and 1,1-dimethylethyl while the term "$(C_{1-6})$alkyl" designates a straight or branched alkyl radical containing up to 6 carbon atoms such as those listed before, pentyl, 1-ethylpropyl, 1-methylbutyl, 1,1-dimethylpropyl, 1,2-dimethylpropyl, 2,2-dimethylpropyl, hexyl, 1-methylpentyl, 4-methylpentyl, 1,3-dimethylbutyl, 3,3-dimethylbutyl and the like. The expression "$(C_{3-6})$alkenyl" identifies straight or branched alkenyl groups containing 3 to 6 carbon atoms and one or two double bonds, such as, 2-propenyl, 1-methyl-2-propenyl, 2-butenyl, 1-methyl-2-butenyl, 2,4-hexadienyl, 1-methyl-2,4-pentadienyl and the like. The term "$(C_{3-6})$alkynyl" designates straight or branched alkynyl group containing 3 to 6 carbon atoms and one or two triple bonds, such as, 2-propynyl, 1-methyl-2-propynyl, 2-butynyl, 1-methyl-2-butynyl, 2,4-hexadiynyl and the like. Th term "$(C_{3-7})$ cycloalkyl" indicates cycloalkyl radicals of 3 to 7 carbon atoms selected from cyclopropyl, cyclobutyl, cyclopentyl, cyclohexyl and cycloheptyl. The expression "$(C_{1-4})$alkoxy" identifies straight or branched alkoxy radicals having at most 4 carbon atoms which are selected from methoxy, ethoxy, propoxy, 1-methylethoxy, butoxy, 1-methylpropoxy, 2-methylpropoxy, 1,1-dimethyletoxy.

The term and the moiety halogen essentially identifies chloro, bromo and fluoro.

A preferred group of compounds comprises those compounds of formula I wherein R stands for $(C_{1-6})$alkyl or $(C_{3-7})$cycloalkyl, $R_1$ and $R_2$, each independently may represent hydrogen, halogen or $(C_{1-4})$alkoxy, $R_3$ stands for hydrogen, methoxy, ethoxy, or mono- or di-methylamino, and $R_4$ represents hydrogen or $(C_{1-4})$alkyl, with the proviso that when simultaneously R stands for ethyl one of $R_1$ and $R_2$ is hydrogen and the other is a methoxy group, and $R_4$ is hydrogen, $R_3$ cannot be a dimethylamino group; and salts therewith of pharmaceutically acceptable salts.

These acid addition salts are obtained by treating compounds of formula I above with pharmaceutically acceptable acids. As acids suitable for the formation of therapeutically acceptable salts there may be mentioned, for example, hydrohalide, sulfuric and phosphoric acids, nitric and perchloric acids; aliphatic, alicyclic, aromatic or heterocyclic carboxylic or sulfonic acids, such as formic, acetic, propionic, succinic, glycolic, lactic, malic, tartaric, citric, ascorbic, maleic, hydroxymaleic, pyruvic acid; phenylacetic, benzoic, para-aminobenzoic, anthranilic, para-hydroxybenzoic, salicyclic, para-aminosalicyclic or embonic acid, methanesulfonic, ethanesulfonic, hydroxyethanesulfonic, ethylenesulfonic acid; halobenzenesulfonic, toluenesulfonic, naphthalenesulfonic acids or sulfanilic acid.

These or other salts of the new compounds may also be used for purifying the resulting compounds by converting them into salts, isolating the latter and liberating the free compound from them. In view of the close relationship between the new compounds in the free form and in the form of their salts what has been said above and hereinafter with reference to the free compounds concerns also the corresponding salts.

A general method for preparing the novel compounds comprises the condensation between a naphthalenediamine of formula II

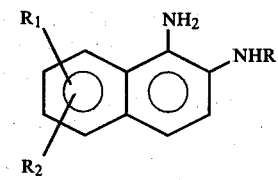

wherein R, $R_1$ and $R_2$ are as defined before, and a suitably selected aldehyde of formula

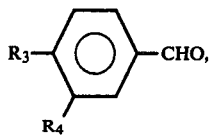

wherein $R_3$ and $R_4$ are as defined before, to yield an intermediate imidazoline which is subsequently oxidized to end product I. The overall reaction is better illustrated in the following scheme A

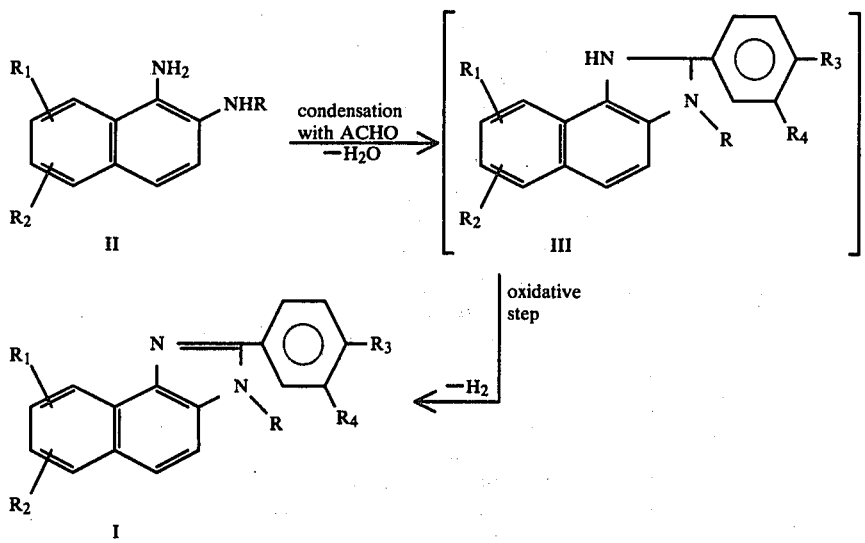

wherein the square brackets mean that the intermediate compound placed within them can be further processed without previous separation.

Widely varying conditions can be used to bring about the condensation between the naphthalenediamine and the aldehyde; however rather good results have been obtained adding an equimolecular proportion or a slight excess of the aldehyde to a solution oof the compound of formula II in an inert high boiling organic solvent such as for instance xylene, toluene, or cymene and then refluxing the obtained reaction mixture in a Dean-Stark apparatus under inert atmosphere.

As for the oxidative step which in the above scheme is visualized as a simple dehydrogenation, it can be performed in the presence of a mild oxidizing agent, such as for instance manganese dioxide or cupric acetate, or better with a dehydrogenating agent suitably selected from the group of metals or metal oxides generally employed and named as "hydrogenating catalysts" such as for instance Palladium, Platinum, Ruthenium, Rhodium, Platinum dioxide, either in powder form or adsorbed on a charcoal or asbestos carrier, and Raney-Nickel. The obtained reaction products are recovered by conventional procedures which involve filtration of the hot solution and evaporation of the solvent under reduced pressure. Purification of the raw material thus obtained is achieved simply by crystallization or by means of chromatographic techniques.

The starting naphthalenediamine derivatives of formula II are generally novel and may be prepared through different routes; for instance, in J. Org. Chem. 37 (22), 3566 (1972), the synthesys of $N^2$-isopropyl-naphthalen-1,2-diamine is reported through (a) nitration of β-naphthaleneamine to 1-nitro-2-naphthaleneamine, (b) exchange of the amino group with a chlorine atom, (c) amination with isopropylamine and finally (d) reduction of the nitro group to amino.

Other methods moreover can be gathered from the literature considering the particular reactivity of the naphthalene substratum.

The process we have generally employed for preparing the starting naphthalenediamine derivatives involves the reduction of a N-substituted-1-nitroso-2-naphthaleneamine of formula

IV

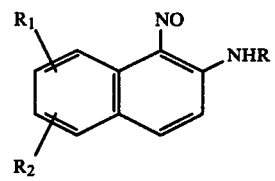

wherein R, $R_1$ and $R_2$ are as defined before, by means of hydrogen gas in the presence of a hydrogenating catalyst. Various hydrogenation catalysts may be employed to bring out the conversion to diamines and generally the same metals and metal oxides employed in the oxidative step of scheme A are preferably used, i.e. Palladium, Platinum, Ruthenium, Rhodium, Platinum dioxide, either in powder form or adsorbed on a carrier, and Raney-nickel. Also the reaction conditions may vary widely since all the catalysts listed above are active, and are preferably used, at room temperature and atmospheric pressure but can suitably be employed also up to 4 atmospheres. Solvents which can conveniently be employed in this reaction are selected from lower aliphatic alcohols such as methanol and ethanol and aromatic hydrocarbons such as for instance benzene, toluene, xylene and cymene.

Alternatively reduction of the N-substituted-1-nitroso-2-naphthalenamine derivative can also be accomplished by using as reducing agents metals such as tin, zinc or aluminum in an acidic medium according to well known procedures.

The starting nitroso compounds have been synthetized according to the method described by S. T. Morgan and F. P. Evens in J. Chem. Soc. 115, 1140 (1919), through acid-catalyzed rearrangement of a 2-(N-nitroso-N-substituted)naphthylamine or more conveniently through reaction of primary amines with 1-nitroso-2-naphthol according to E. W. Malmberg and C. S. Hamilton in J. Am. Chem. Soc. 70, 2415 (1948).

The above reported method for preparing the starting naphthalenediamines II from the corresponding N-substituted-1-nitroso-2-naphthaleneamines is of particular value for many reasons. First of all in fact the reduction reaction does not require drastic conditions but on the contrary it proceeds rapidly at room temperature and atmospheric pressure, secondly the reaction conditions themselves, the solvents and the starting nitroso-compounds employed are particularly safe from the industrial point of view; thirdly the naphthalenediamines thus obtained are not necessarily separated from the reaction mixture and the condensation with the suitably selected aldehyde can be carried out without any working up of the reaction mixture containing the hydrogenated compound of formula II before adding the aldehyde. In this case, if separation of the naphthalenediamines is not required, also the reduction of the N-substituted-1-nitroso-2-naphthaleneamines will be carried out in an inert high-boiling organic solvent.

Moreover, since catalyzed reduction, which takes place on the catalyst's surface, is a reversible process, the same catalysts employed for reducing the nitrosonaphthaleneamines can be conveniently employed in the absence of hydrogen, in the dehydrogenation procedure. The interaction between a naphthalenediamine of formula II and an acid derivative which may be an acyl chloride, anhydride or ester provides another convenient route to the naphthoimidazoles of the present invention. More particularly, the naphthalenediamine is contacted with a compound of formula

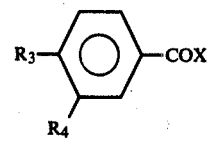

wherein $R_3$ and $R_4$ are as defined before and X may represent a chlorine atom,
a group $—OR_5$ wherein $R_5$ may be the same radical

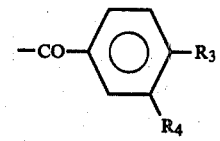

or a trifluoroacetyl, ethoxycarbonyl or alkyl sulfonyl moiety or,
a group $—OR_6$ wherein $R_6$ is a methyl or ethyl radical.

This two step reaction involves formation of a monoacylated naphthalenediamine as the key intermediate according to the following scheme B:

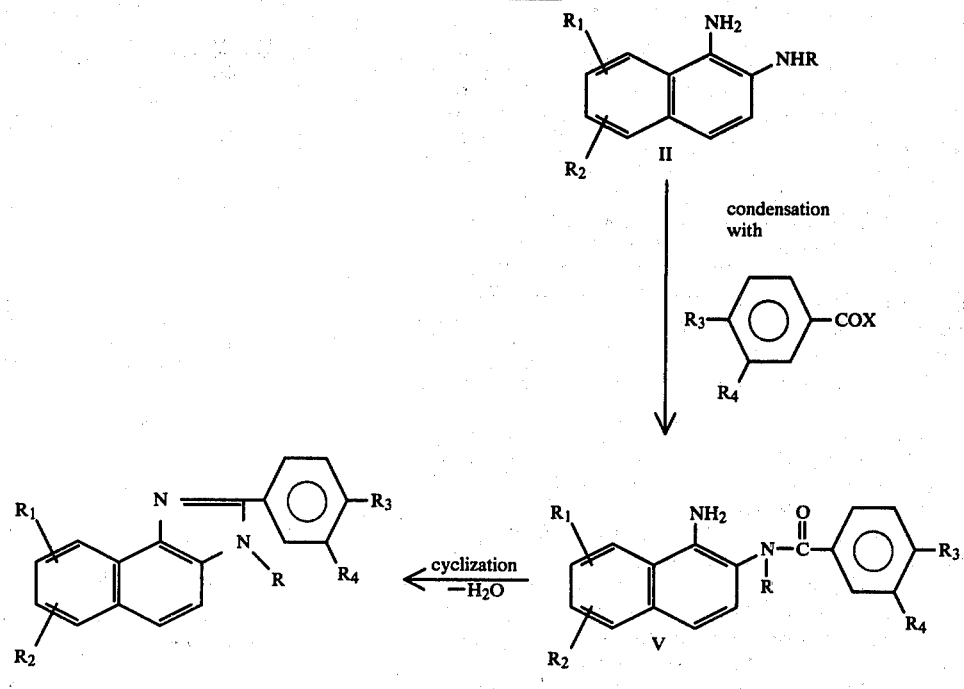

As for the first step which leads to the intermediate mono-acylated compounds, we found that high yields can be realized when an equimolecular mixture of a naphthalendiamine II and an acid derivative

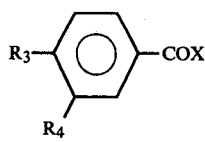

is dissolved in an anhydrous inert organic solvent selected from lower aliphatic halogenated and aromatic hydrocarbons in the presence of a tertiary organic nitrogen base which should block the inorganic or organic acid which forms during the course of the reaction.

Finally, conversion of the mono-acylated intermediate to the desired end product, through elimination of water, is carried out by refluxing it in an inert organic solvent optionally in the presence of an acidic catalyst such as sulphuric or p-toluenesulphonic acid. Recovery and purification of the end naphthoimidazoles, involves the same conventional procedures already described in the first process. Furthermore some compounds of formula I may be obtained also through chemical modifications of other compounds, falling within the same formula I, prepared according to one of the reaction schemes outlined before. For instance, compounds wherein $R_3$ is methoxy or ethoxy are conveniently prepared by reaction of the corresponding hydroxyphenyl derivatives with suitable agents such as methyl or ethyl, halogenides, tosylates or mesylates.

A convenient route leading to monomethylamino phenyl compounds in high yields consists in preparing the sodium derivative of the amidic nitrogen atom of a corresponding acylamino derivative prepared according to the general methods described before, then substituting it by means of an alkylating agent and finally splitting off the protecting acyl group by alkaline hydrolysis. It is intended that alternative methods which can suitably be employed for transforming a pre-existing radical into another falling within the given meanings, although not specifically disclosed, are to be considered within the scope of the present invention.

As stated before, the novel compounds of the present invention are active as antiinflammatories, mild analgesics and mild antipyretics. These biological activietes are coupled with a lox toxicity since the approximate $LD_{50}$s per os in mice are generally higher than 500 mg/kg. The toxicities were determined according to Lichtfield and Wilcoxon, Journ. Pharm. Expt. Ther., 96, 99, (1949).

The antiinflammatory activity was ascertained by means of several testing methods; in one, the ability of the compounds of the invention to reduce the edema induced in the rat paw by injection of carrageenin was evaluated and the test was performed according to the methodology described by C. A. Winter et al. in Proc. Soc. Exptl. Biol. Med. 111, 544, (1962).

In another it was investigated the reduction by the test compounds of the weight of the granuloma formed on a cotton pellet implanted subcutaneously in rats, following the method described by Meier et al. in Experimentia, 6, 469, (1950).

In still another some of the compounds were tested in the adjuvant induced arthritis test in rats.

This test which was performed as described by B. B. Newbold in Bri. Journ. Pharmacol., 21, 127, (1963), is absolutely meaningful, because adjuvant arthritis is one of the best pharmacological tool with which a pharmacologist can investigate compounds as to their possible antiinflammatory activity, owing to the fact that this experimental model of chronic inflammation looks closer like to the conditions of rheumatoid arthritis of the human pathology (see Pearson, C. M., Arthritis and allied conditions, page 119, Lea and Febiger Publ. 1967 and Pearson C. M., J. Chronic Diseases, 16, 863 (1963).

The compounds were administered to the rats at different dose levels generally corresponding to about one twentieth or one twentyfifth, one tenth and one fifth (the highest dose) of the corresponding toxic doses expressed in $LD_{50}$ values. However, even if the $LD_{50}$ values of the compounds to be tested are higher than 1000 mg/kg, the maximum dose level at which they are administered is generally never higher than 200 mg/kg. These dosages are quite far from the toxic dose. Actually, in the carrageenin-induced oedema test, used as a preliminary screening test, the compounds to be tested were first administered at the highest dose level which, as stated above, corresponds to one fifth of the $LD_{50}$ value or 200 mg/kg if the $LD_{50}$ value is higher than 1000 mg/kg. The compounds displaying an interesting degree of antiinflammatory activity i.e. those causing a percent decrease of the induced edema of about 40 or more, were further tested at lower dosages and then submitted to the granuloma pellet test. The results obtained in these tests are reported in the following Table I:

TABLE I

| Compound of Example No. | $LD_{50}$ os | Dose mg/kg os | Percent inhibition of the carrageenin-induced edema | Percent inhibition of the granuloma pellet |
|---|---|---|---|---|
| 1 | 1000 | 50 | 24 | — |
|  |  | 100 | 37 | — |
|  |  | 200 | 42 | 24 |
| 2 | >1000 | 50 | 21 | — |
|  |  | 100 | 37 | — |
|  |  | 200 | 45 | 40 |
| 3 | ~1000 | 50 | 34 | — |
|  |  | 100 | 41 | — |
|  |  | 100 | 53 | 40 |
| 4 | 500 | 20 | 32 | — |
|  |  | 50 | 46 | — |
|  |  | 100 | 54 | 24 |
| 5 | 500 | 20 | 35 | — |
|  |  | 50 | 50 | — |
|  |  | 100 | 64 | 38 |
| 7 | 500 | 20 | 29 | — |
|  |  | 50 | 37 | — |
|  |  | 100 | 47 | 33 |
| 9 | >1000 | 50 | 32 | — |
|  |  | 100 | 45 | — |
|  |  | 200 | 48 | 45 |
| 15 | >1000 | 20 | 31 | — |
|  |  | 50 | 45 | — |
|  |  | 100 | 49 | — |
|  |  | 200 | 52 | 31 |

The compounds of examples 3, 5 and 9 which gave the best results in the carrageenin-induced edema and in the granuloma pellet tests, were then further tested in the adjuvant arthritis test at a dosage corresponding to 1/5 of their $LD_{50}$ or at 200 mg/kg if the $LD_{50}$ is higher than 1000. The measure of effectiveness of the compounds in this test is given by their ability in reducing the volume of the hind paws of the rats. The results obtained are collected in Table II below:

TABLE II

| Compound of Example No. | Dose mg/kg rats p.o. | % Reduction of the volume of the hind paws over the control |
| --- | --- | --- |
| 3 | 200 | 33 |
| 5 | 100 | 42 |
| 9 | 200 | 53 |

These favorable characteristics are coupled also with interesting analgesic and antipyretic properties which were investigated according to the methods described by Randall et al. in Arch. Int. Pharmacodyn. 111, 409, (1957) and by Buller et al. in J. Pharm. Pharmacol. 9, 128, (1957) respectively. It is finally to be noted that the new naphthoimidazoles which are the object of the present invention display a very low ulcerogenic activity which is several times lesser than the one observed with other known and therapeutically used antiinflammatory substances. The ulcerogenic action was determined according to Thuillier et al. Chim. Ther. 3, 51, (1968).

The use of the novel compounds as antiinflammatory agents which is a further specific object of the present invention refers to all industrially applicable aspects and acts of said use including the embodying of the novel compounds or their salts into pharmaceutical compositions.

For antiinflammatory use the compounds of the invention may be administered by different routes. While the preferred routes of administration are oral and rectal, parenteral administration can also be employed. For oral administration the compounds of the present invention are compounded into pharmaceutical dosage forms such as for instance tablets, capsules, elixirs, solutions and the like. Tablets may contain in addition to the therapeutic ingredient the usual additives such inert diluents, for example starch, lactose, kaolin, calcium phosphate, mannitol and the like; binders, for example gelatin, starch, sugars, gums, carboxymethylcellulose, polyvinylpyrrolidone, and the like; lubricants, for example talc, magnesium stearate, stearic acid and the like; and the commonly employed disintegrant, coloring, sweetening and flavoring agents. Coated or hard-shell capsules may also be prepared which may contain the same additives indicated above for tablets. Liquid preparations such as elixirs and solutions are prepared by dissolving the active ingredient in an aqueous or non-aqueous pharmaceutically acceptable solvent and may contain also suspending sweetening, flavoring and preservative agents as known in the art.

For rectal administration the compounds are formulated as suppositories wherein the active ingredient is admixed with conventional vehicles such as for example cocoa butter, wax, spermaceti or polyoxyethylenglycols and their derivatives.

The dosage range is from about 0.05 to about 10.0 g. per day, preferably administered in divided doses. Accordingly, the present invention provides a pharmaceutical composition for antiinflammatory use comprising from about 50 to about 1000 mg of a compound of the invention as the active ingredient together with a pharmaceutically acceptable carrier.

The following examples illustrate the process of the invention and describe in detail some compounds of general formula I without limiting the scope of the invention.

EXAMPLE 1

3-methyl-2-phenyl-3H-naphtho[1,2-d]imidazole 11.35 g of benzoyl chloride (0.08 mole) dissolved in 50 cc of methylene chloride is added to a solution of 14.57 g of $N^2$-methylnaphthalene-1,2-diamine (0.084 mole) and 11.3 cc of triethylamine (0.08 mole) in 100 cc of methylene chloride, and the obtained reaction mixture is allowed to stand at room temperature for about one hour. Then it is heated to the reflux temperature for 16 hours, cooled to room temperature and filtered over bleaching earth. The filtrate is diluted with 200 cc of methylene chloride, washed twice with water, once with 5% sodium bicarbonate and then with water up to neutral reaction of the aqueous phase. The methylene chloride solution, dried over sodium sulphate, is concentrated to dryness yielding a residue which taken up with 300 cc of benzene is then poured into a 500 cc flask equipped with a Dean Stark apparatus. 0.18 g of p-toluensulphonic acid is gradually added to this solution heated to the reflux temperature. After 4 hours, the reaction mixture is cooled to room temperature and filtered. The filtrate washed with water, is dried over sodium sulphate and then concentrated to dryness yielding 13.1 g of the compound of the title. M.p. 127°–28° C. (from ethanol).

EXAMPLE 2

3-methyl-2-(4-ethoxyphenyl)-3H-naphtho[1,2-d]imidazole

A solution of 11.16 g (0.06 mole) of 2-methylamino-1-nitrosonaphthalene in 800 cc of toluene is hydrogenated at room temperature and at the atmospheric pressure in the presence of 3 g of Palladium-on-carbon. After one hour, when the theoretical amount of hydrogen has been consumed, 9 cc (0.06 mole) of 4-ethoxy benzaldehyde are added and the obtained reaction mixture is heated to the reflux temperature under an inert atmosphere for about 3 hours. The water which forms during the reaction distillates as binary azeotrope with toluene and is separated through a Dean-Stark apparatus. Then further 1.5 g of 5% Palladium-on-carbon are added and reflux is prolonged for two additional hours. Filtration of the hot solution followed by concentration of the filtrate to dryness under vacuum affords a residue which has been purified by cristallization from ethyl acetate. Yield 14.5 g (80%) M.p. 138°–9° C.

EXAMPLES 3 TO 6

The following compounds are prepared by operating according to the procedures of the foregoing example, by hydrogenating the starting N-methyl-1-nitroso-naphthalenamine, condensing the obtained diamino compound with a suitable selected aldehyde and then dehydrogenating the resulting imidazoline derivative.

(3)  2-(4-methoxyphenyl)-3-methyl-3H-naphtho[1,2-d]imidazole. M.p. 132°–134° C. (from ethyl acetate)

(4)  N,N-dimethyl-4-(3-methyl-3H-naphtho[1,2-d]imidazol-2-yl) benzenamine. M.p. 136°–8° C. (from benzene)

(5)  4-(3-methyl-3H-naphtho[1,2-d]imidazol-2-yl)-2,N,N-trimethylbenzenamine. M.p. 116°–118° C. (from methyl-t.butyl ether)

(6)  3-methyl-2-(3-methyl-4-methoxyphenyl)-3H-naphtho[1,2-d]imidazole. M.p. 104°–105° C. (from diisopropyl ether).

EXAMPLE 7

N-methyl-4-(3-methyl-3H-naphtho[1,2-d]imidazol-2-yl)benzenamine 5 g of N-[4-(3-methyl-3H-naphtho[1,2-d]imidazol-2-yl)phenyl]acetamide prepared by following the procedure described in example 2 but using 4-formylphenyl)acetamide instead of 4-ethoxy-benzaldehyde are dissolved in 80 cc of anhydrous dimethylformamide and to the obtained solution, cooled to a temperature comprised between 0° C. and 5° C., 0.09 g of 55% NaH are gradually added. After 1½ hour when the evolution of hydrogen gas ceases 1 cc of methyl jodide dissolved in 20 cc of dimethylformamide is dripped in the reaction mixture is allowed to reach room temperature. Then the solution is poured into 1 lt. of water and stirred for about 20 minutes; the solid which precipitates is recovered by filtration and dried under vacuum yielding 4.53 g of a mixture of two products one of which does correspond to the desacetylated product.

This mixture is dissolved in 300 cc of methyl alcohol and 200 cc of 10% NaOH and refluxed for 6 hours; then methanol is distilled off at atmospheric pressure and the reaction mixture is cooled and diluted with water. The precipitate which forms is recovered by filtration and crystallized from benzene yielding 3.6 g of the compound of the title which melts at 225°-227° C.

EXAMPLE 3

4-3-methyl-3H-naphtho[1,2-d]imidazol-2-yl)phenol

This compound is prepared according to the procedures described under Example 2 but using 4-hydroxybenzaldehyde instead of 4-ethoxybenzaldehyde. M.p. >300° C. (from acetic acid).

EXAMPLE 9

3-(1-methylethyl)-2-(4-methoxyphenyl)-3H-naphth[1,2-d]imidazole

In a multi-necked 500 cc flask equipped with a mechanical stirrer and a Dean Stark apparatus a solution of 2 g (0.01 mole) of $N^2$-(1-methylethyl)naphthalendiamine (known from J. Org. Chem. 37 (22), 3566 (1972)), 1.36 g (0.01 mole) of 4-methoxybenzaldehyde and 300 cc of toluene are heated at the reflux temperature under argon atmosphere for 3 hours. Then 2 g of 5% Palladium on carbon are added and the reaction mixture is heated at the reflux temperature for further three hours. Upon filtering off the catalyst, the filtrate is taken to small volume yielding 2.86 g of a raw product which is recovered by filtration and purified by crystallization from ethyl acetate. From the mother liquors taken to dryness further 1.7 g are obtained which are chromatographed through a silicagel column eluting with benzene: ethyl acetate 95:5. Overall yield 57%. M.p. 162°-63° C.

The compound of the title is also prepared by following the same procedure described in example 2 but starting from N-isopropyl-1-nitroso-2-naphthaleneamine instead of N-methyl-1-nitroso-2-naphthaleneamine and using 4-methoxybenzaldehyde instead of 4-ethoxybenzaldehyde. Yield 60% M.p. 162°-63° C. (from ethyl acetate).

The starting N-isopropyl-1-nitroso-2-naphthaleneamine is prepared through reaction of 1-nitroso-2-naphthol with isopropylamine according to the method described in J. Am. Chem. Soc. 70, 2415 (1948).

EXAMPLE 10

3-butyl-2-(4-methoxyphenyl)-3H-naphtho[1,2-d]imidazole

The compound of the title is prepared by following essentially the same procedure described in example 2 but starting from 2-butylamino-1-nitrosonaphthalene instead of 2-methylamino-1-nitrosonaphthalene and employing 4-methoxybenzaldehyde instead of 4-ethoxybenzaldehyde. Yield 53%. M.p. 99,5°-100,5° C.

EXAMPLE 11

8-methoxy-2-(4-methoxyphenyl)-3-methyl-3H-naphtho[1,2-d]imidazole hydrochloride

The compound of the title, as the free base, is prepared by following essentially the same procedure described in example 2 but using 7-methoxy-2-methylamino-1-nitrosonaphthalene instead of 2-methylamino-1-nitrosonaphthalene and 4-methoxybenzaldehyde instead of 4-ethoxybenzaldehyde. By addition of HCl to a diethyl ether solution of the free base, the corresponding hydrochloride precipitates. Yield 40%. M.p. 265° C. dec. (from methanol).

EXAMPLE 12

7-methoxy-2-(4-methoxyphenyl)-3-methyl-3H-naphtho[1,2-d]imidazole hydrochloride

The compound of the title is prepared by following essentially the same procedure described in the foregoing example but starting from 6-methoxy-2-methylamino-1-nitrosonaphthalene instead of 7-methoxy-2-methylamino-1-nitrosonaphthalene. Yield 35%. M.p. 261° C. (from methanol). The starting 6-methoxy-2-methylamino-1-nitrosonaphthalene is prepared by adding 3.75 g of 6-methoxy-1-nitroso-2-naphthol to a solution of 9.5 cc of 35% $CH_3NH_2$ in 15 cc of water cooled to about 10° C., heating the reaction mixture to 40° C. for a few minutes and finally recovering the solid which precipitates on cooling to room temperature.

EXAMPLE 13

6-chloro-7-methoxy-2-(4-methoxyphenyl)-3-methyl-3H-naphth[1,2-d]imidazole

The compound of the title is prepared by following essentially the same procedure described in example 2 but starting from 5-chloro-6-methoxy-2-methylamino-1-nitrosonaphthalene instead of 2-methylamino-1-nitrosonaphthalene and employing 4-methoxybenzaldehyde instead of 4-ethoxybenzaldehyde. Yield 48%. M.p. 247°-48° C. (from ethanol). The starting 5-chloro-6-methoxy-2-methylamino-1-nitrosonaphthalene is prepared through reaction of methylamine with 5-chloro-6-methoxy-1-nitroso-2-naphthol following the procedure described in the second portion of the foregoing example. In its turn this last compound is prepared by nitrosation of 5-chloro-6-methoxy-2-naphthol obtained from (5-chloro-6-methoxy-2-naphthalenyl)-ethanone which is a commercial product.

EXAMPLE 14

3-cyclohexyl-2-(4-metoxyphenyl)-3H-naphth[1,2-d]imidazole hydrochloride

The compound of the title is prepared by following essentially the same procedure described in example 11 but using 2-cyclohexlamine-1-nitrosonaphthalene instead of 7-methoxy-2-methylamino-1-nitrosonaphthalene. Yield 76%. M.p. 238° C. dec.

The starting 2-cyclohexylamine-1-nitrosonaphthalene is prepared by reacting 1-nitroso-2-naphthol with cyclohexylamine according to the procedure described in the second part of example 12.

EXAMPLE 15

3-ethyl-2-(4-methoxyphenyl)-3H-naphtho[1,2-d]imidazole

The compound of the title is prepared according to the procedure described in example 2 but starting from 2-ethylamino-1-nitrosonaphthalene instead of 2-methylamino-1-nitrosonaphthalene and adding 4-methoxybenzaldehyde instead of 4-ethoxybenzaldehyde. Yield 81%. M.p. 144°–146° C. (from ethyl acetate).

The starting 2-ethylamino-1-nitrosonaphthalene is prepared by reacting 1-nitroso-2-naphthol with ethylamine following the same procedure described in the second part of example 12.

By operating according the procedures of the foregoing examples the following compounds may be prepared:

3-(1-ethylpropyl)-2-(4-methoxyphenyl)-3H-naphtho[1,2-d]imidazole
3-cyclobutyl-2-(4-methoxyphenyl)-3H-naphtho[1,2-d]imidazole
3-cyclopropyl-2-(4-methoxyphenyl)-3H-naphtho[1,2-d]imidazole
3-cyclopentyl-2-(4-methoxyphenyl)-3H-naphtho[1,2-d]imidazole
3-cyclohepyl-2-(4-methoxyphenyl)-3H-naphtho[1,2-d]imidazole
3-(2-propenyl)-2-(4-methoxyphenyl)-3H-naphtho[1,2-d]imidazole
3-(1,1-dimethylethyl)-2-(4-methoxyphenyl)-3H-naphtho[1,2-d]imidazole
3-(1-methylpropyl)-2-(4-methoxyphenyl)-3H-naphtho[1,2-d]imidazole
3-(1-ethylpropyl)-2-(4-methoxyphenyl)-3H-naphtho[1,2-d]imidazole
3-(1-methyl-2-propenyl)-2-(4-methoxyphenyl)-3H-naphtho[1,2-d]imidazole
3-(2-propynyl)-2-(4-methoxyphenyl)-3H-naphtho[1,2-d]imidazole
6-chloro-3-methyl-2-phenyl-3H-naphtho[1,2-d]imidazole
3-ethyl-7,8-dimethoxy-2-phenyl-3H-naphtho[1,2-d]imidazole
7-chloro-3-methyl-2-phenyl-3H-naphtho[1,2-d]imidazole
8-chloro-3-methyl-2-phenyl-3H-naphtho[1,2-d]imidazole
7-methoxy-3-methyl-2-phenyl-3H-naphtho[1,2-d]imidazole
8,9-dichloro-3-ethyl-2-phenyl-3H-naphtho[1,2-d]imidazole
3-ethyl-2-phenyl-3H-naphtho[1,2-d]imidazole
2-phenyl-3-propyl-3H-naphtho[1,2-d]imidazole
3-(1-methylethyl)-2-phenyl-3H-naphtho[1,2-d]imidazole
3-butyl-2-phenyl-3H-naphtho[1,2-d]imidazole
N,N-dimethyl-4-(3-ethyl-3H-naphtho[1,2-d]imidazol-2-yl)-benzenamine
2-(3-methyl-4-methoxyphenyl)-3-ethyl-3H-naphtho[1,2-d]imidazole
N-methyl-4-(3-ethyl-3H-naphtho[1,2-d]imidazol-2-yl)benzenamine
N-methyl-4-(7-methoxy-3-methyl-3H-naphtho[1,2-d]imidazol-2-yl)-benzenamine
4-methoxy-2-(4-methoxyphenyl)-3-methyl-3H-naphtho[1,2-d]imidazole
5-methoxy-2-(4-methoxyphenyl)-3-methyl-3H-naphtho[1,2-d]imidazole
6-methoxy-2-(4-methoxyphenyl)-3-methyl-3H-naphtho[1,2-d]imidazole
9-methoxy-2-(4-methoxyphenyl)-3-methyl-3H-naphtho[1,2-d]imidazole
3-ethyl-7-methoxy-2-(4-methoxyphenyl)-3H-naphtho[1,2-d]imidazole
3-butyl-7-methoxy-2-(4-methoxyphenyl)-3H-naphtho[1,2-d]imidazole
2-(4-methoxyphenyl)-3-methyl-7-methylthio-3H-naphtho[1,2-d]imidazole
7-ethylthio-3-methyl-2-phenyl-3H-naphtho[1,2-d]imidazole
2-(4-methoxyphenyl)-3,7-dimethyl-3H-naphtho[1,2-d]imidazole
7-chloro-2-(4-methoxyphenyl)-3-methyl-3H-naphtho[1,2-d]imidazole
7-ethoxy-2-(4-methoxyphenyl)-3-methyl-3H-naphtho[1,2-d]imidazole
7-ethyl-2-(4-methoxyphenyl)-3-methyl-3H-naphtho[1,2-d]imidazole
2-(4-methoxyphenyl)-3-methyl-7-(1-methylethyl)-3H-naphtho[1,2-d]imidazole
7-trifluoromethoxy-2-(4-methoxyphenyl)-3-methyl-3H-naphtho[1,2-d]imidazole
6-chloro-7-methoxy-3-methyl-2-phenyl-3H-naphtho[1,2-d]imidazole
6-chloro-3-ethyl-7-methoxy-2-(4-methoxyphenyl)-3H-naphtho[1,2-d]imidazole
4-(7-methoxy-3-methyl-3H-naphtho[1,2-d]imidazol-2-yl)-2,N,N-trimethylbenzenamine
4-(7,8-dimethoxy-3-methyl-3H-naphtho[1,2-d]imidazol-2-yl)-2,N,N-trimethylbenzenamine
4-(3-ethyl-7-methoxy-3H-naphtho[1,2-d]imidazol-2-yl)-2,N,N-trimethylbenzenamine

EXAMPLE 39

A tablet is prepared from

| 2-(4-methoxyphenyl)-3-(1-methylethyl)-3H—naphth[1,2-d]imidazole | 500 mg |
|---|---|
| starch | 40 mg |
| talc | 10 mg |
| magnesium stearate | 10 mg |

EXAMPLE 40

A tablet is prepared from

| 2-(4-methoxyphenyl)-3-methyl-3H—naphth[1,2-d]imidazole | 300 mg |
|---|---|
| lactose | 50 mg |
| microcrystalline cellulose | 50 mg |
| stearic acid | 10 mg |
| colloidal silica | 5 mg |

EXAMPLE 41

A capsule is prepared from

| | |
|---|---|
| 4-(3-methyl-3H—naphth[1,2-d]imidazol-2-yl)-2,N,N—trimethylbenzenamine | 400 mg |
| talc | 40 mg |
| sodium carboxymethylcellulose | 40 mg |
| starch | 120 mg |

We claim:

1. A 3H-naphtho[1,2-d]imidazole derivative having the following formula

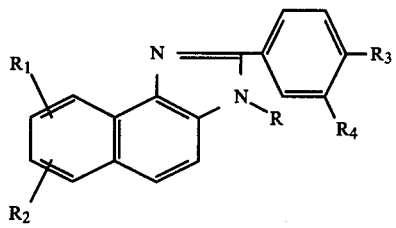

wherein R stands for $(C_{1-6})$alkyl, $(C_{3-6})$alkenyl, $(C_{3-6})$alkynyl or $(C_{3-7})$cycloalkyl, $R_1$ and $R_2$ each independently may represent hydrogen, halogen $(C_{1-4})$alkyl, $(C_{1-4})$alkylthio, $(C_{1-4})$alkoxy or halo$(C_{1-4})$alkoxy, $R_3$ stands for hydrogen, methoxy, ethoxy or mono- or di-methylamino, and $R_4$ represents hydrogen or $(C_{1-4})$alkyl with the proviso that when simultaneously R stands for an ethyl radical, one of $R_1$ and $R_2$ is hydrogen and the other one is a methoxy group and $R_4$ is hydrogen, $R_3$ cannot be a dimethylamino group; or a non-toxic pharmaceutically acceptable acid addition salt thereof.

2. A compound as in claim 1 wherein R stands for $(C_{1-6})$alkyl or $(C_{3-4})$cycloalkyl, $R_1$ and $R_2$ each independently represent hydrogen, halogen or $(C_{1-4})$alkoxy, $R_3$ stands for hydrogen, methoxy, ethoxy, or mono- or di-methylamino, and $R_4$ represents hydrogen or $(C_{1-4})$alkyl, with the proviso that when simultaneously R stands for ethyl, one of $R_1$ and $R_2$ is hydrogen and the other is a methoxy group, and $R_4$ is hydrogen, $R_3$ cannot be a dimethylamino group; or a non-toxic pharmaceutically acceptable acid addition salt thereof.

3. A compound of claim 1 which is 2-(4-methoxyphenyl)-3-(1-methylethyl)-3H-naphtho[1,2-d]imidazole.

4. A compound of claim 1 which is 2-(4-methoxyphenyl)-3-methyl-3H-naphtho[1,2-d]imidazole.

5. A compound of claim 1 which is 4-(3-methyl-3H-naphtho[1,2-d]imidazol-2-yl)-2,N,N-trimethylbenzenamine.

6. A 3H-naphtho[1,2-d]imidazole derivative having the following formula

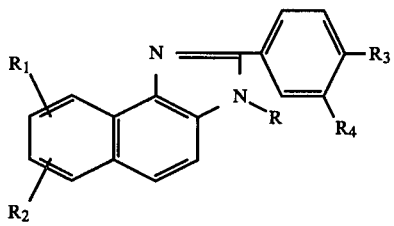

wherein R represents $(C_{1-6})$alkyl, $(C_{3-6})$alkenyl, $(C_{3-6})$alkynyl or $(C_{3-7})$cycloalkyl, $R_1$ and $R_2$ each independently represents hydrogen, halogen $(C_{1-4})$alkyl, $(C_{1-4})$alkylthio, $(C_{1-4})$alkoxy or halo$(C_{1-4})$alkoxy, $R_3$ represents hydrogen, methoxy or ethoxy and $R_4$ represents hydrogen or $(C_{1-4})$alkyl or a non-toxic pharmaceutically-acceptable acid addition salt thereof.

7. A compound as claimed in claim 6 wherein R represents $(C_{1-6})$alkyl or $(C_{3-7})$cycloalkyl, $R_1$ and $R_2$ each independently represents hydrogen, halogen or $(C_{1-4})$alkoxy, $R_3$ represents hydrogen, methoxy or ethoxy, and $R_4$ represents hydrogen or $(C_{1-4})$alkyl, or a non-toxic pharmaceutically-acceptable acid addition salt thereof.

8. A 3H-naphtho[1,2-d]imidazole derivative having the following formula

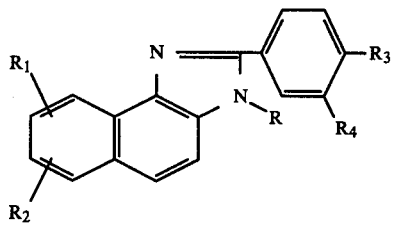

wherein R represents $(C_{1-6})$alkyl, $(C_{3-6})$alkenyl, $(C_{3-6})$alkynyl or $(C_{3-7})$cycloalkyl, $R_1$ and $R_2$ each independently represents hydrogen, halogen $(C_{1-4})$alkyl, $(C_{1-4})$alkylthio, $(C_{1-4})$alkoxy or halo$(C_{1-4})$alkoxy, $R_3$ represents mono- or di-methylamino, and $R_4$ represents hydrogen or $(C_{1-4})$alkyl, with the proviso that when simultaneously R represents an ethyl radical, one of $R_1$ and $R_2$ is hydrogen and the other one is methoxy group and $R_4$ is hydrogen, $R_3$ cannot be a dimethylamino group; or a non-toxic pharmaceutically-acceptable acid addition salt thereof.

9. A compound as claimed in claim 8 wherein R represents $(C_{1-6})$alkyl or $(C_{3-7})$cycloalkyl, $R_1$ and $R_2$ each independently represents hydrogen, halogen or $(C_{1-4})$alkoxy, $R_3$ represents mono- or di-methylamino, and $R_4$ represents hydrogen or $(C_{1-4})$alkyl, with the proviso that when simultaneously R represents an ethyl, one of $R_1$ and $R_2$ is hydrogen and the other is a methoxy group, and $R_4$ is hydrogen, $R_3$ cannot be a dimethylamino group; or a non-toxic pharmaceutically-acceptable acid addition salt thereof.

10. A composition useful for antiinflammatory use which comprises from about 50 to about 1000 mg of a compound of formula I

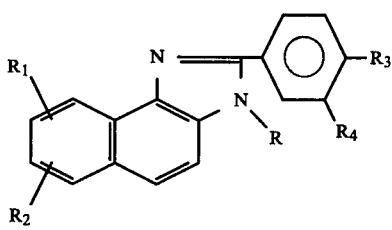

wherein R, $R_1$, $R_2$, $R_3$, and $R_4$ are as defined in claim 1 or a salt therewith of a pharmaceutically acceptable acid, in admixture with a pharmaceutical carrier.

11. A composition useful for antiinflammatory use which comprises from about 50 to about 1000 mg of a compound of the following formula

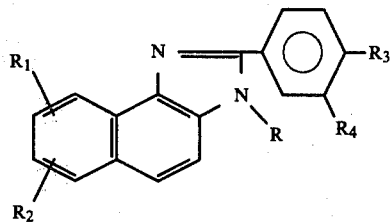

wherein R, $R_1$, $R_2$, $R_3$, and $R_4$ are as defined in claim 6; or a salt therewith of a pharmaceutically-acceptable acid; in admixture with a pharmaceutical carrier.

12. A composition useful for antiinflammatory use which comprises from about 50 to about 1000 mg of a compound of the following formula

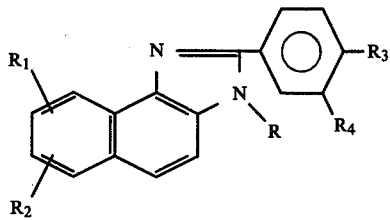

wherein R, $R_1$, $R_2$, $R_3$, and $R_4$ are as defined in claim 8, or a salt therewith of a pharmaceutically-acceptable acid; in admixture with a pharmaceutical carrier.

13. A method for relieving antiinflammatory diseases in animals which comprises administering to an animal in need thereof an amount comprised between about 0.05 to about 10.00 g per day of a compound of formula I

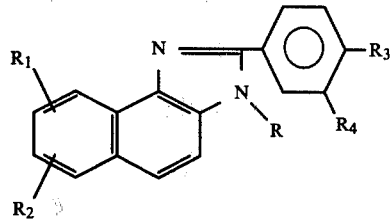

wherein R, $R_1$, $R_2$, $R_3$, and $R_4$ are as defined in claim 1 or a salt therewith of a pharmaceutically acceptable acid.

14. A method for relieving antiinflammatory diseases in animals which comprises administering to an animal in need thereof an amount comprised between about 0.05 to about 10.00 g per day of a compound of the following formula

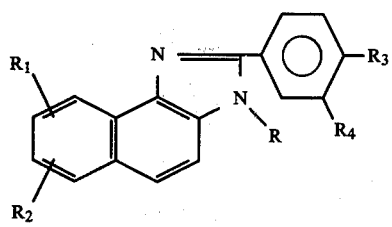

wherein R, $R_1$, $R_2$, $R_3$, and $R_4$ are as defined in claim 6; or a salt therewith of a pharmaceutically-acceptable acid.

15. A method for relieving antiinflammatory diseases in animals which comprises administering to an animal in need thereof an amount comprised between about 0.05 to about 10.00 g per day of a compound of the following formula

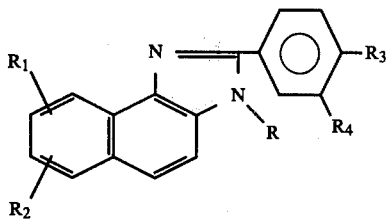

wherein R, $R_1$, $R_2$, $R_3$ and $R_4$ are as defined in claim 8, or a salt therewith of a pharmaceutically-acceptable acid.

* * * * *